(12) United States Patent
Breton et al.

(10) Patent No.: US 6,544,533 B2
(45) Date of Patent: Apr. 8, 2003

(54) 10-HYDROXY-2-DECENOIC ACID COMPOUNDS FOR PROMOTING DESQUAMATION/EPIDERMAL RENEWAL OF THE SKIN AND/OR COMBATING SKIN AGING

(75) Inventors: Lionel Breton, Versailles (FR); Nathalie Pineau, Poitiers (FR); Emile Benechie, Gif (FR); Martine Li, Le Plessis Robinson (FR); Françoise Picot, Chevreuse (FR); Pierre Potier, Paris (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/811,424

(22) Filed: Mar. 20, 2001

(65) Prior Publication Data

US 2002/0012684 A1 Jan. 31, 2002

Related U.S. Application Data

(63) Continuation of application No. PCT/FR99/02230, filed on Sep. 20, 1999.

(30) Foreign Application Priority Data

Sep. 22, 1998 (FR) ............................................. 98 11810

(51) Int. Cl.$^7$ ........................... A61K 7/00; A61K 7/075; A61K 9/107; A61K 9/14; A61K 9/20; A61K 9/48

(52) U.S. Cl. ...................... 424/401; 424/70.1; 424/439; 424/451; 424/464; 424/489; 514/844; 514/937; 514/944; 514/945; 514/962

(58) Field of Search .................................. 424/401, 489, 424/70.1, 47; 514/549, 844, 845, 846, 847, 848, 937, 944, 945

(56) References Cited

FOREIGN PATENT DOCUMENTS

EP 0 989 111 A1 * 3/2000

OTHER PUBLICATIONS

CAPLUS abstract of EP 989111 A1, (Maignan et al.), Cosmetic compositions containing derivatives of 10–hydroxy–2–decenoic acid for desquamation of the skin, AN 2000:209663, Mar. 2000.*
CAPLUS abstract of JP 10147514 A2, (Takimoto et al.), Skin or hair cosmetics, AN 1998:351496, Jun. 1998.*

* cited by examiner

Primary Examiner—Russell Travers
Assistant Examiner—Alysia Berman
(74) Attorney, Agent, or Firm—Burns, Doane, Swecker & Mathis, L.L.P.

(57) ABSTRACT

10-Hydroxy-2-decenoic acid compounds, particularly the 10-hydroxydec-2-enoates, are well suited for promoting desquamation of human skin and/or stimulating epidermal renewal and thus combating intrinsic and/or extrinsic cutaneous aging.

13 Claims, No Drawings

10-HYDROXY-2-DECENOIC ACID COMPOUNDS FOR PROMOTING DESQUAMATION/EPIDERMAL RENEWAL OF THE SKIN AND/OR COMBATING SKIN AGING

CROSS-REFERENCE TO PRIORITY/PCT APPLICATIONS

This application claims priority under 35 U.S.C. §119 of FR-98/11810, filed Sep. 22, 1998, and is a continuation of PCT/FR-99/02230, filed Sep. 20, 1999 and designating the United States (and was not published by the International Bureau in English on Mar. 30, 2000 as WO 00/16739), both hereby expressly incorporated by reference.

BACKGROUND OF THE INVENTION

1. Technical Field of the Invention

The present invention relates to the administration of effective amounts of at least one 10-hydroxy-2-decenoic acid compound/composition for promoting desquamation of the skin and/or to stimulate epidermal renewal and/or to combat aging of the skin.

The compounds/compositions of this invention are especially well suited for promoting desquamation of the skin and/or for stimulating epidermal renewal and, therefore, for combating intrinsic and/or extrinsic cutaneous aging, as well as for the nontherapeutic treatment of the skin to promote desquamation and/or to combat aging of the skin.

2. Description of the Prior Art

Desquamation is a natural phenomenon associated with the fact that the epidermis, which constitutes the upper layer of the skin, is continually being regenerated. The epidermis is composed of several layers of cells, the deepest of which is the basal layer consisting of undifferentiated cells. Over time, these cells differentiate and migrate towards the surface of the epidermis, constituting the various layers thereof, until they form at the surface of the epidermis the corneocytes, which are dead cells which are removed by desquamation. This loss at the surface is compensated for by the migration of cells from the basal layer towards the surface of the epidermis. There is perpetual renewal of the skin. Forced removal of the horny layer accelerates this renewal and thus permits the combating of skin aging.

At the same time, these cells continue their differentiation, the final stage of which is the corneocyte. These are dead cells which constitute the final layer of the epidermis, namely, the outermost layer, also known as the stratum corneum.

Cutaneous aging resulting from intrinsic or extrinsic factors is reflected by the appearance of wrinkles and fine lines, by yellowing of the skin, which develops a parchment-like look accompanied by the appearance of pigmentary blemishes, by the disorganization of the elastin and collagen fibers, resulting in a loss of elasticity, of flexibility and of firmness, or by the appearance of telangiectases.

Certain of these signs of aging are more particularly associated with intrinsic or physiological aging, namely, with "normal" aging, related to age, or chronobiological aging, whereas others are more specific to extrinsic aging, namely, aging caused, in general, by the environment; this relates more particularly to photoaging due to exposure to the sun, to light or to any other radiation.

The present invention relates to intrinsic or physiological aging, as well as to extrinsic aging.

The changes in the skin due to intrinsic aging are the consequence of a genetically programmed senescence involving endogenous factors. This intrinsic aging results, in particular, in a slowing down of the renewal of the cells of the skin, which is reflected essentially by the appearance of detrimental clinical changes, such as a reduction in the subcutaneous adipose tissue and the appearance of small wrinkles or fine lines, and by histopathological changes, such as an increase in the number and thickness of elastic fibers, a loss of vertical fibers from the membrane of the elastic tissue, and the presence of large irregular fibroblasts in the cells of this elastic tissue.

In contrast, extrinsic aging causes detrimental clinical changes, such as large wrinkles and the formation of a flaccid and weathered skin, and histopathological changes, such as an excessive accumulation of elastic material in the upper dermis and degeneration of the collagen fibers.

Various active agents for combating cutaneous aging are known to the prior art.

Thus, U.S. Pat. No. 4,603,146 describes formulating retinoic acid and derivatives thereof into cosmetic compositions for combating cutaneous aging.

Moreover, numerous patents and publications (see, for example, EP-A-413,528) describe, and numerous commercial cosmetic compositions contain, α-hydroxy acids, such as lactic acid, glycolic acid or citric acid, for treating cutaneous aging.

Too, β-hydroxy acids, and more especially salicylic acid and derivatives thereof are known for their desquamating properties (see WO A 93/10756 and U.S. Pat. No. 4,767, 750).

All of the aforesaid prior art compounds elicit action against aging of the skin by promoting desquamation, i.e., the removal of the "dead" cells located at the surface of the horny layer of the epidermis. This "desquamating" property is also referred to, often incorrectly, as a keratolytic property.

However, the prior art compounds also present objectionable side effects, such as stinging, stabbing pains, sensations of heat and red blotches which are unpleasant for the user.

Need therefore continues to exist for antiaging agents exhibiting activity which is at least as effective as that of the compounds of the prior art, but without their disadvantages.

SUMMARY OF THE INVENTION

Accordingly, a major object of the present invention is the provision of active agents for promoting desquamation of the skin and/or stimulating epidermal renewal, while at the same time avoiding the stinging, stabbing pains, sensations of heat or red blotches which are unpleasant for the user and which to date have characterized the state of this art.

Briefly, it has now surprisingly and unexpectedly been determined that administration of effective amounts of 10-hydroxy-2-decenoic acid compounds promotes desquamation of the skin and/or stimulates epidermal renewal and thus combats skin aging.

Certain 10-hydroxy-2-decenoic acid derivatives are known to the prior art as activators of the immune system.

It was heretofore unknown, however, that the 10-hydroxy-2-decenoic acid compounds were useful for promoting desquamation of the skin and/or stimulating epidermal renewal and thus combating intrinsic and/or extrinsic cutaneous aging.

The present invention thus features formulating effective amounts of 10-hydroxy-2-decenoic acid compounds having the formulae described below into composition suited for promoting desquamation of the skin and/or stimulating epidermal renewal and thus combating intrinsic and/or extrinsic cutaneous aging.

DETAILED DESCRIPTION OF BEST MODE AND SPECIFIC/PREFERRED EMBODIMENTS OF THE INVENTION

More particularly according to the present invention, the subject 10-hydroxy-2-decenoic acid compounds advantageously have the following formulae:

(a) 2-dimethylaminoethyl 10-hydroxydec-2-enoate having the formula:

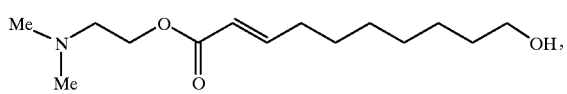

(b) 2,3-dihydroxypropyl 10-hydroxydec-2-enoate having the formula:

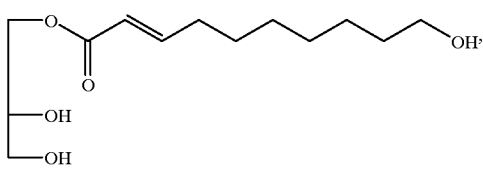

(c) 2-hydroxypropyl 1,3-di(10-hydroxydec-2-enoate) having the formula:

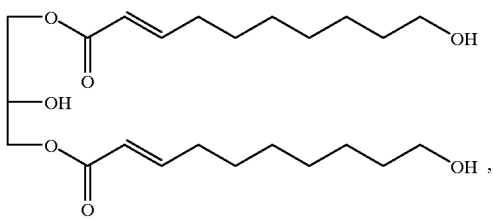

(d) propyl 1,2,3-tri(10-hydroxydec-2-enoate) having the of formula:

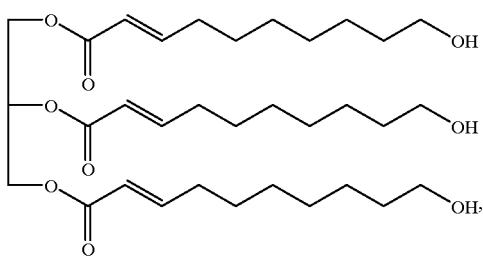

and (e) 3-[(2-methoxyethoxy)methoxy]propyl 1,2-di(1o-hydroxydec-2-enoate) having the formula:

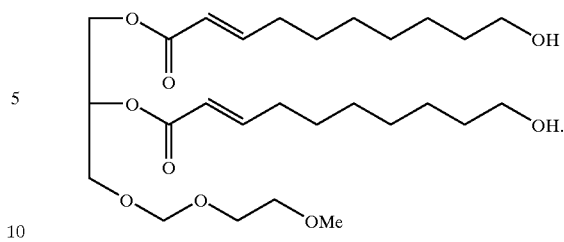

By the term 10-hydroxy-2-decenoic acid compound or derivative are intended the purified compounds described above, of natural or synthetic origin, or any preparation comprised thereof.

And by the term "natural origin" is intended a compound extracted from natural material in which it is present. By the term "synthetic origin" is intended a compound prepared by chemical synthesis or by biotechnology.

It is of course envisaged to administer the 10-hydroxy-2-decenoic acid compounds alone, or in any admixture thereof.

Likewise, the 10-hydroxy-2-decenoic acid derivatives can be administered in their cis and/or trans form.

The amounts of the 10-hydroxy-2-decenoic acid derivatives/compounds administered according to the invention very obviously depend on the desired effect and must be an amount which is effective for promoting desquamation of the skin and/or stimulating epidermal renewal and thus combating intrinsic and/or extrinsic cutaneous aging.

For example, the amount of the 10-hydroxy-2-decenoic acid compound administered according to the invention advantageously ranges from 0.001% to 10% and preferably from 0.01% to 1% by weight of the total weight of the composition.

This invention thus features compositions for promoting desquamation of the skin and/or stimulating epidermal renewal and thus combating intrinsic and/or extrinsic cutaneous aging which comprise at least one 10-hydroxy-2-decenoic acid derivative/compound, formulated into a cosmetically/dermatologically acceptable vehicle, diluent or carrier therefor.

In the compositions according to the invention, the 10-hydroxy-2-decenoic acid derivative/compound is advantageously present in an amount of 0.001% to 10% and preferably of 0.01% to 1% by weight of the total weight of the composition.

The present invention also features a nontherapeutic regime/regimen for promoting desquamation of the skin and/or stimulating epidermal renewal and thus combating intrinsic and/or extrinsic cutaneous aging, comprising administering to an individual subject in need of such treatment, a thus-effective amount of at least one 10-hydroxy-2-decenoic acid compound.

The subject compositions are advantageously topically applied onto the skin and can be provided in any known pharmaceutical dosage form, such as, for example, in the form of an emulsion, in particular an oil-in-water or water-in-oil emulsion, indeed even in the form of a multiple emulsion.

Same can also be provided in the form of an aqueous solution, optionally a gel solution, or in the form of a lotion, for example a two-phase lotion, of a cream, of a milk or indeed even of a foam.

The compositions of the invention can be ingested, injected or topically applied to the skin (over any cutaneous region of the body), hair, nails or mucous membranes (buccal, jugal, gingival, genital or connective). Depending on the method or mode of administration, the compositions according to the invention can be provided in all of the pharmaceutical dosage forms normally employed.

For topical application onto the skin, the subject compositions can have the form, in particular, of an aqueous or oily solution or of a dispersion of the lotion or serum type, of emulsions with a liquid or semi-liquid consistency of the milk type, obtained by dispersion of a fatty phase in an aqueous phase (O/W) or vice versa (W/O), or of suspensions or emulsions with a soft consistency of the aqueous or anhydrous gel or cream type, or, alternatively, of microcapsules or microparticles, or of vesicular dispersions of ionic and/or nonionic type. These compositions are formulated according to conventional techniques.

The subject compositions can also be used for the hair in the form of aqueous, alcoholic or aqueous/alcoholic solutions, or in the form of creams, gels, emulsions or foams or, alternatively, in the form of aerosol compositions also comprising a pressurized propellant. The compositions according to the invention can also be hair care compositions and, in particular, a shampoo, a hair setting lotion, a treating lotion, a styling cream or gel, a dyeing composition (in particular oxidation dyeing composition), optionally in the form of coloring shampoos, hair restructuring lotions, a permanent wave composition (in particular a composition for the first step of permanent waving), a lotion or gel for combating hair loss, an antiparasitic shampoo, and the like.

For administration by injection, the composition can be provided in the form of an aqueous or oily lotion or in the form of a serum. For the eyes, it can be provided in the form of drops and, for ingestion, it can be provided in the form of capsules, granules, syrups or tablets.

The amounts of the various constituents of the compositions according to the invention are those conventionally employed in the fields under consideration.

The compositions according to the invention can also be solid preparations constituting cleansing soaps or bars.

The compositions can also be packaged in the form of an aerosol composition, also comprising a pressurized propellant.

When the composition is an emulsion, the proportion of the fatty phase advantageously ranges from 5% to 80% by weight and preferably from 5% to 50% by weight with respect to the total weight of the composition. The oils, waxes, emulsifiers and coemulsifiers contained in the composition in the form of an emulsion are selected from among those conventionally employed in the cosmetics field. The emulsifier and the coemulsifier are typically included in the composition in a proportion ranging from 0.3% to 30% by weight and preferably from 0.5 to 20% by weight with respect to the total weight of the composition. In addition, the emulsion can contain lipid vesicles.

When the composition is an oily solution or gel, the fatty phase can constitute more than 90% of the total weight of the composition.

The compositions of the invention are suited for cosmetic or pharmaceutical applications. The compositions of the invention are preferably cosmetic compositions.

In known fashion, the subject cosmetic/dermatological compositions can also contain the usual cosmetic adjuvants, additives and such as hydrophilic or lipophilic gelling agents, hydrophilic or lipophilic additives, and active agents, preservatives, antioxidizing agents, solvents, fragrances, fillers, UV-screening agents, odor absorbers and colorants. The amounts of these various additives and adjuvants are those conventionally employed in the cosmetics field and advantageously range, for example, from 0.01% to 10% of the total weight of the composition. These additives and adjuvants, depending on their nature, can be formulated into the fatty phase, into the aqueous phase and/or into the lipid spherules. Exemplary oils or waxes according to the invention include mineral oils (liquid petrolatum), vegetable oils (liquid fraction of karite butter, sunflower oil), animal oils (perhydrosqualene), synthetic oils (purcellin oil), silicone oils or waxes (cyclomethicone) and fluorinated oils (perfluoropolyethers), beeswax, carnauba wax and paraffin wax. Fatty alcohols and fatty acids (stearic acid) can be added to these oils.

Exemplary emulsifiers according to the invention include, for example, glycerol stearate, polysorbate 60 and the PEG-6/PEG-32/Glycol Stearate mixture marketed under the trademark Tefoses® 63 by Gattefosse.

Exemplary solvents according to the invention include lower alcohols, in particular ethanol and isopropanol, or propylene glycol.

And exemplary hydrophilic gelling agents according to the invention include carboxyvinyl polymers (carbomer), acrylic copolymers, such as acrylate/alkyl acrylate copolymers, polyacrylamides, polysaccharides, such as hydroxypropylcellulose, natural gums and clays and exemplary lipophilic gelling agents include modified clays, such as bentones, metal salts of fatty acids, such as aluminum stearates, and hydrophobic silica, ethylcellulose and polyethylene.

The subject compositions can also contain other hydrophilic active principles or bioaffecting active agents, such as proteins or protein hydrolysates, amino acids, polyols, urea, allantoin, sugars and sugar derivatives, water-soluble vitamins, plant extracts and hydroxy acids.

Exemplary lipophilic active principles or agents that can be included are, for example, retinol (vitamin A) and derivatives thereof, tocopherol (vitamin E) and derivatives thereof, essential fatty acids, ceramides, essential oils, or salicylic acid and derivatives thereof.

According to the present invention, the subject compositions can be an admixture of at least one compound of formula (I) with at least one other active agent. Exemplary such other active agents include:

(a) agents which improve the activity with respect to hair regrowth and/or with respect to slowing down or retarding hair loss and which are already known for this activity, such as, for example, nicotinic acid esters, including, in particular, tocopherol nicotinate, benzyl nicotinate and nicotinates of $C_1$–$C_6$ alkyls, such as methyl or hexyl nicotinates, pyrimidine derivatives, such as 2,4-diamino-6-piperidinopyrimidine 3-oxide or "Minoxidil", described in U.S. Pat. Nos. 4,139,619 and 4,596,812, or agents which promote hair regrowth, such as those described in the European patent application published under the number 0,648,488 (assigned to the assignee hereof);

(b) agents which vary cutaneous pigmentation and/or proliferation and/or differentiation, such as retinoic acid and isomers thereof, retinol and esters thereof, vitamin D and derivatives thereof, estrogens, such as estradiol, kojic acid or hydroquinone;

(c) antibacterials, such as clindamycin phosphate, erythromycin or antibiotics of the tetracycline class;

(d) agents for combating parasites, in particular metronidazole, crotamiton or pyrethroids;

(e) antifungals, in particular compounds belonging to the imidazole class, such as econazole, ketoconazole or miconazole, or salts thereof, polyene compounds, such as amphotericin B, compounds of the allylamine family, such as terbinafine, or alternatively octopirox;

(f) antiviral agents, such as acyclovir;

(g) steroidal anti-inflammatory agents, such as hydrocortisone, betamethasone valerate or clobetasol propionate, or nonsteroidal anti-inflammatory agents, such as, for example, ibuprofen and salts thereof, diclofenac and salts thereof, acetylsalicylic acid, acetaminophen or glycyrrhizic acid;

(h) anaesthetic agents, such as lidocaine hydrochloride and derivatives thereof;

(i) antipruritic agents, such as thenaldine, trimeprazine or cyproheptadine;

(j) keratolytic agents, such as α- and β-hydroxycarboxylic acids or β-ketocarboxylic acids, their salts, amides or esters and, more particularly, hydroxy acids, such as glycolic acid, lactic acid, salicylic acid, citric acid and the fruit acids generally, and 5-(n-octanoyl)salicylic acid;

(k) agents for combating free radicals, such as α-tocopherol or esters thereof, superoxide dismutases, certain metal chelating agents or ascorbic acid and esters thereof;

(l) antiseborrhoeic agents, such as progesterone;

(m) antidandruff agents, such as octopirox or zinc pyrithione;

(n) antiacne agents, such as retinoic acid or benzoyl peroxide;

(o) extracts of plant, marine or bacterial origin.

Other biologically active compounds can also be included in the above list, namely, for example, diazoxide, spiroxazone, phospholipids, such as lecithin, linoleic and linolenic acids, salicylic acid and derivatives thereof described in FR-2,581,542, such as salicylic acid derivatives substituted by an alkanoyl group having from 2 to 12 carbon atoms in the 5-position of the benzene ring, hydroxycarboxylic or ketocarboxylic acids and esters thereof, lactones and their corresponding salts, anthralin, carotenoids, eicosatetraenoic and eicosatrienoic acids or esters and amides thereof, vitamin D and derivatives thereof, or extracts of plant or bacterial origin.

Thus, in one embodiment, the subject compositions according to the invention also comprise at least one active agent selected from among antibacterial agents, agents for combating parasites, antifungals, antivirals, anti-inflammatories, antipruritics, anaesthetics, keratolytics, agents for combating free radicals, antiseborrhoeics, antidandruff agents, antiacne agents and/or agents which decrease cutaneous pigmentation and/or proliferation and/or differentiation, or extracts of plant, marine or bacterial origin.

The pharmaceutical compositions according to the invention can be administered parenterally, enterally or topically. These pharmaceutical composition are preferably administered topically.

In order to further illustrate the present invention and the advantages thereof, the following specific examples are given, it being understood that same are intended only as illustrative and in nowise limitative.

EXAMPLE 1

In this example, the ability of 10-hydroxy-2-decenoic acid derivatives to promote desquamation was evaluated.

This test of in vitro screening of an agent which is active with regard to desquamation was carried out on differentiated human keratinocytes. The principle of the test is based on the fact that desquamation induces the release of corneocytes. The desquamating power of the test product increases as the number of corneocytes released increases.

The protocol of the test was as follows: beginning with biopsies of human skin, the keratinocytes obtained by separation from the epidermis were dissociated by enzymatic action with trypsin and were cultured at a concentration of $2 \cdot 10^5$ cell/ml. The growth and differentiation of the keratinocytes was obtained by culturing for 10 to 20 days in a specific medium. The activity of the test product was then evaluated after removal of the culture medium. To accomplish this, two samples were taken at T0 and T60, namely, before the addition of the test product and 60 minutes after this addition. The samples thus taken were analyzed with a flow cytometer in order to count the population of corneocytes. The flow cytometer made it possible to distinguish the populations of corneocytes and of keratinocytes by treatment with acridine orange, which is specific for cellular DNA. This staining is specific for the keratinocytes, since normal corneocytes do not have nuclei and therefore do not contain DNA.

The cellular detachment index was determined by the difference between T60 and T0. The same measurement was carried out for a control not comprising test product, because the experiment inevitably produces the release of corneocytes, even in the absence of active principles.

The test was carried out with compounds at a concentration of $5 \cdot 10^{-5}$ M.

The following compounds were tested: propyl 1,2,3-tri (10-hydroxydec-2-enoate), and 3-[(2-methoxyethoxy) methoxy]propyl 1,2-di(10-hydroxydec-2-enoate).

The results of this study are reported in the following Table:

TABLE

| Compounds at $5 \cdot 10^{-5}$ M | %** |
|---|---|
| Reference* | 91.95 |
| Propyl 1,2,3-tri(10-hydroxydec-2-enoate) | 148.52 |
| 3-[(2-Methoxyethoxy)methoxy]propyl 1,2-di (10-hydroxydec-2-enoate) | 124.16 |

*Reference: 2-Hydroxy-5-octanoylbenzoic acid, which is known to promote desquamation (see FR-85/06,953 assigned to the assignee hereof)
**% of activity with respect to the control composed of an identical culture in the absence of compound.

These results evidence that the activity of the subject derivatives with respect to cellular detachment was indeed high.

The following are specific examples of formulations according to the present invention. These compositions were formulated by simple intimate admixing of the various components thereof.

EXAMPLE 2

| Composition 1 - Milk for the face: | |
|---|---|
| Liquid petrolatum | 7.0 g |
| 3-[(2-Methoxyethoxy)methoxy]propyl 1,2-di(10-hydroxydec-2-enoate) | 1.0 g |
| Glyceryl monostearate, polyethylene glycol stearate (100 EO) | 3.0 g |
| Carboxyvinyl polymer | 0.4 g |
| Stearyl alcohol | 0.7 g |
| Soya bean proteins | 3.0 g |
| NaOH | 0.4 g |
| Preservative | q.s. |
| Water | q.s. for 100 g |

This composition was formulated as a milk for the face, had good cosmetic properties and was soft and comfortable upon application.

The pH of this composition was approximately 5.5.

EXAMPLE 3

| Composition 2 - Lotion: | |
| --- | --- |
| 2-Hydroxypropyl 1,3-di(10-hydroxydec-2-enoate) | 0.5 g |
| 2-Ethylhexyl palmitate | 10.0 g |
| Cyclopentadimethylsiloxane | 20.0 g |
| Butylene glycol | 5.0 g |
| Preservative | q. s. |
| Water | q.s. for 100 g |

This lotion, which did not contain surfactant, promoted desquamation of the skin.

EXAMPLE 4

| Composition 3 - Milk: | |
| --- | --- |
| Octyl palmitate | 35.0 g |
| Glycerol | 2.0 g |
| Propyl 1,2,3-tri(10-hydroxydec-2-enoate) | 2.0 g |
| $C_{10}$–$C_{30}$ Acrylates/alkyl acrylates crosslinked polymer | 0.1 g |
| Triethanolamine | 0.1 g |
| Wheat amino acids | 1.0 g |
| Preservative | q.s. |
| Water | q.s. for 100 g |

The milk obtained, which did not contain surfactant, had good cosmetic properties.

EXAMPLE 5

| Composition 4 - Gel for the face: | |
| --- | --- |
| Glycerol | 10.0 g |
| 3-[(2-Methoxyethoxy)methoxy]propyl 1,2-di(10-hydroxydec-2-enoate) | 2.0 g |
| Disodium cocoamphodiacetate | 1.0 g |
| Preservative | q.s. |
| Water | q.s. for 100 g |

The gel obtained had good cosmetic properties.

EXAMPLE 6

| Composition 5 - Gel for cleansing with water: | |
| --- | --- |
| Butylene glycol | 7.0 g |
| Sodium lauroyl sarcosinate | 4.0 g |
| Propyl 1,2,3-tri(10-hydroxydec-2-enoate) | 5.0 g |
| Triethanolamine | 0.8 g |
| Carbomer | 0.5 g |
| Preservative | q.s. |
| Water | q.s. for 100 g |

The gel obtained had good cosmetic properties.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A cosmetic/dermatological regime/regimen for promoting desquamation of the skin and/or stimulating epidermal renewal and thus combating intrinsic and/or extrinsic cutaneous aging, comprising administering to an individual subject in need of such treatment, a thus-effective amount of at least one 10-hydroxydec-2-enoate selected from the group consisting of:

(a) 2-dimethylaminoethyl 10-hydroxydec-2-enoate having the formula:

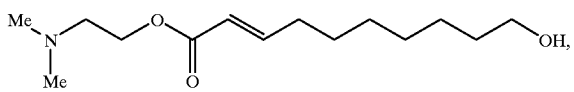

(b) 2,3-dihydroxypropyl 10-hydroxydec-2-enoate having the formula:

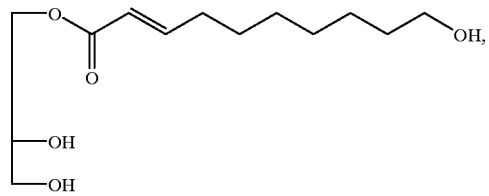

(c) 2-hydroxypropyl 1,3-di(10-hydroxydec-2-enoate) having the formula:

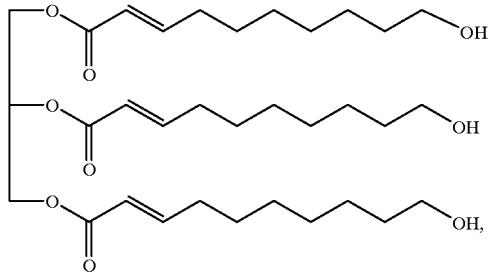

(d) propyl 1,2,3-tri(10-hydroxydec-2-enoate) having the formula:

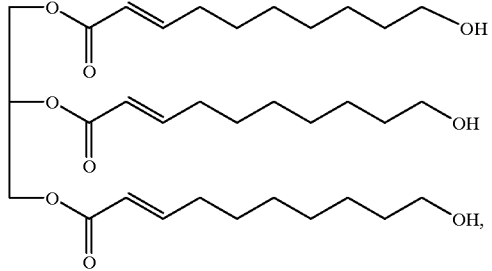

and (e) 3-[(2-methoxyethoxy)methoxy]propyl 1,2-di(10-hydroxy-dec-2-enoate) having the formula:

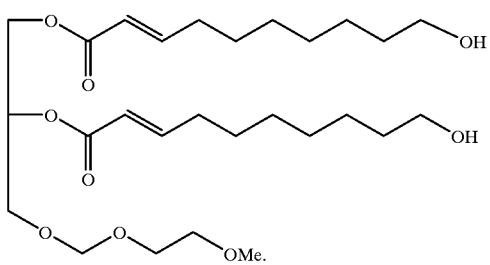

wherein the cosmetic/dermatological regime/regimen is administered by topical application, ingestion or injection.

2. A cosmetic/dermatological composition suited for promoting desquamation of human skin and/or stimulating epidermal renewal and thus combating intrinsic and/or extrinsic cutaneous aging, comprising a desquamation/epidermal renewal-effective amount of at least one 10-hydroxydec-2-enoate, selected from the group consisting of:

(a) 2-dimethylaminoethyl 10-hydroxydec-2-enoate having the formula:

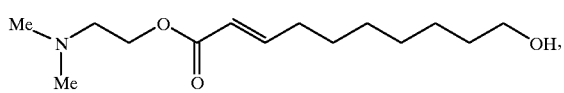

(b) 2,3-dihydroxypropyl 10-hydroxydec-2-enoate having the formula:

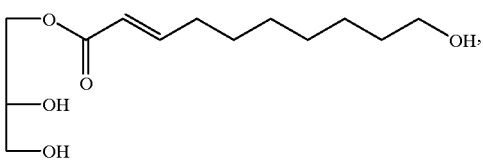

(c) 2-hydroxypropyl 1,3-di(10-hydroxydec-2-enoate) having the formula:

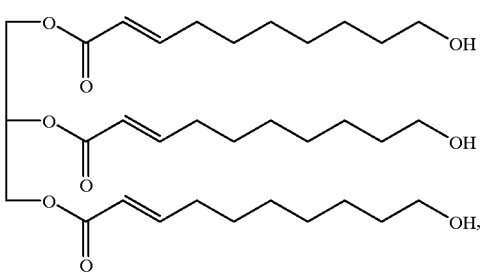

(d) propyl 1,2,3-tri(10-hydroxydec-2-enoate) having the formula:

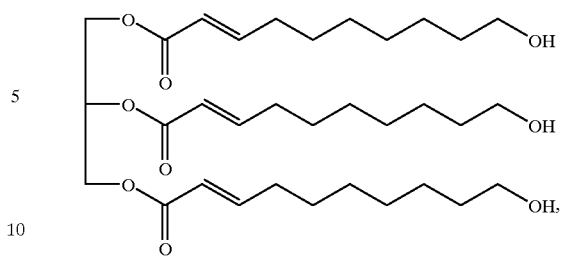

and (e) 3-[(2-methoxyethoxy)methoxy]propyl 1,2-di(10-hydroxy-dec-2-enoate) having the formula:

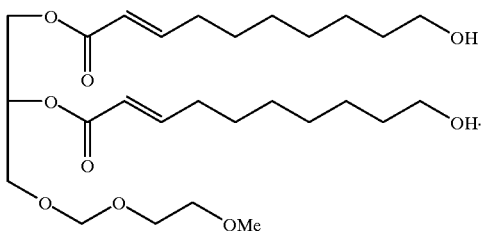

formulated into a cosmetically/dermatologically acceptable vehicle, diluent or carrier thereof.

3. A topically applicable cosmetic/dematological composition suited for promoting desquamation of human skin and/or stimulating epidermal renewal and thus combating intrinsic and/or extrinsic cutaneous aging, comprising a desquamation/epidermal renewal-effective amount of at least one 10-hydroxydec-2-enoate, selected from the group consisting of:

(a) 2-dimethylaminoethyl 10-hydroxydec-2-enoate having the formula:

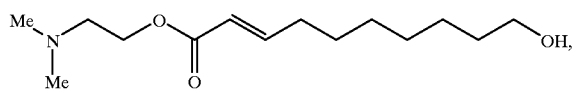

(b) 2,3-dihydroxypropyl 10-hydroxydec-2-enoate having the formula:

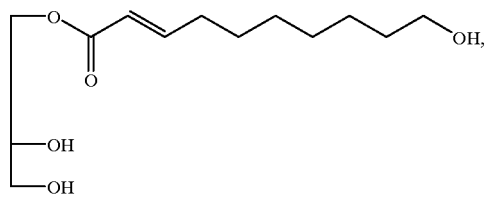

(c) 2-hydroxypropyl 1,3-di(10-hydroxydec-2-enoate) having the formula:

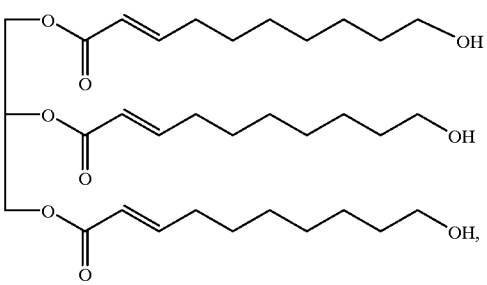

(d) propyl 1,2,3-tri(10-hydroxydec-2-enoate) having the formula:

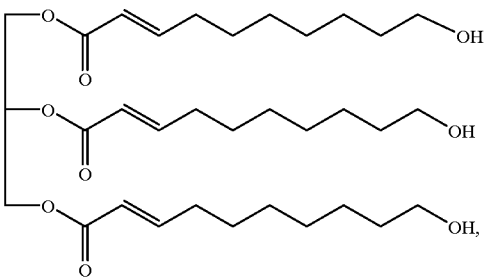

and (e) 3-[(2-methoxyethoxy)methoxy]propyl 1,2-di(10-hydroxy-dec-2-enoate) having the formula:

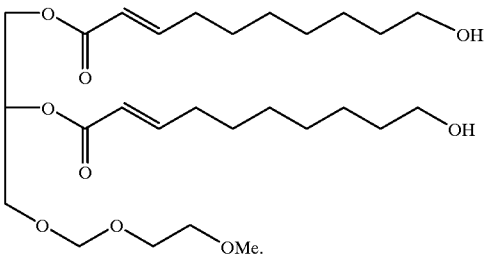

formulated into a topically applicable, cosmetically/dermatologically acceptable vehicle, diluent or carrier thereof.

4. The cosmetic/dermatological composition as defined by claim 2, comprising from 0.001% to 10% by weight of said at least one 10-hydroxydec-2-enoate.

5. The cosmetic/dermatological composition as defined by claim 4, comprising from 0.01% to 1% by weight of said at least one 10-hydroxydec-2-enoate.

6. The topically applicable cosmetic/dermatological composition as defined by claim 3, formulated as an emulsion, a gel, an aqueous solution, a cream, a milk, a lotion, a foam, a solid, a vesicular dispersion, microcapsules or microparticles, a shampoo, or as an aerosol.

7. The cosmetic/dermatological composition as defined by claim 2, formulated as an injectable.

8. The cosmetic/dermatological composition as defined by claim 2, formulated as eyedrops.

9. The cosmetic/dermatological composition as defined by claim 2, formulated for ingestion.

10. The cosmetic/dermatological composition as defined by claim 9, formulated as capsules, granules, tablets, or as a syrup.

11. The cosmetic/dermatological composition as defined by claim 2, further comprising a hydrophilic or lipophilic gelling agent, a hydrophilic or lipophilic bioaffecting active agent, a preservative, an antioxidant, a solvent, a fragrance, a filler, a UV-sunscreen, an odor absorber, a colorant, or combination thereof.

12. The cosmetic/dermatological composition as defined by claim 2, further comprising an antibacterial agent, an agent for combating parasites, an antifungal, an antiviral, an anti-inflammatory, an antipruritic, an anaesthetic, a keratolytic, an agent for combating free radicals, an antiseborrhoeic, an antidandruff agent, an antiacne agent, and agent which decreases cutaneous pigmentation and/or proliferation and/or differentiation, an extract of plant, marine or bacterial origin, an agent affecting hair growth/loss, diazoxide, spiroxazone, a phospholipid, linoleic acid, linolenic acid, salicylic acid or derivative thereof, a lactone or salt thereof, anthralin, a carolenoid, eicosatetraenoic acid or eicosatrienoic acid or ester or amide thereof, or combination thereof.

13. The cosmetic/dermatological regime/regimen as defined by claim 1, carried out without any sensation of stinging, stabbing pain, heat and/or red blotching.

* * * * *